(12) United States Patent
Senetar et al.

(10) Patent No.: US 9,399,603 B2
(45) Date of Patent: Jul. 26, 2016

(54) INCREASED CONVERSION OF RECYCLED OXYGENATES IN MTO

(71) Applicant: UOP LLC, Des Plaines, IL (US)

(72) Inventors: John J. Senetar, Naperville, IL (US); Daniel A. Kauff, Arlington Heights, IL (US); Andrea G. Bozzano, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 249 days.

(21) Appl. No.: 14/089,104

(22) Filed: Nov. 25, 2013

(65) Prior Publication Data

US 2015/0148575 A1     May 28, 2015

(51) Int. Cl.
*C07C 1/22*     (2006.01)
*C07C 1/20*     (2006.01)

(52) U.S. Cl.
CPC .......................................... *C07C 1/20* (2013.01)

(58) Field of Classification Search
CPC ....................................................... C07C 1/20
USPC .................................. 585/638, 639, 640, 641
See application file for complete search history.

(56) References Cited

U.S. PATENT DOCUMENTS

| | | | |
|---|---|---|---|
| 3,978,150 A | | 8/1976 | McWilliams |
| 5,026,935 A | | 6/1991 | Leyshon |
| 5,026,936 A | | 6/1991 | Leyshon |
| 5,914,433 A | | 6/1999 | Marker |
| 6,166,282 A | * | 12/2000 | Miller ........................ C07C 1/20 585/638 |
| 6,858,133 B2 | | 2/2005 | Dath |
| 6,867,341 B1 | | 3/2005 | Abrevaya |
| 7,087,155 B1 | | 8/2006 | Dath |
| 7,268,265 B1 | | 9/2007 | Stewart |
| 7,375,257 B2 | | 5/2008 | Dath |
| 2004/0064007 A1 | * | 4/2004 | Beech .................... B01J 8/0055 585/639 |
| 2008/0039670 A1 | * | 2/2008 | Miller ........................ C07C 1/20 585/639 |
| 2011/0301393 A1 | * | 12/2011 | Stevens ..................... B01J 8/26 585/324 |

* cited by examiner

*Primary Examiner* — In Suk Bullock
*Assistant Examiner* — Sharon Pregler

(57) ABSTRACT

A process is presented for increasing the conversion efficiency of oxygenates to olefins. The conversion of oxygenates recycles unconverted oxygenates and oxygenate by-products to a second reactor unit. The present of oxygenate by-products decreases the efficiency of the methanol to olefins reaction, and passing recycled oxygenates to a second reactor unit maintains the methanol to olefins conversion efficiency while converting the by-products in a secondary zone.

19 Claims, 4 Drawing Sheets

US 9,399,603 B2

INCREASED CONVERSION OF RECYCLED OXYGENATES IN MTO

FIELD OF THE INVENTION

The present invention is the process for conversion of oxygenates to olefins. In particular, the oxygenates to olefins process uses a new reactor design for increasing the conversion of oxygenates to olefins.

BACKGROUND

The traditional method of olefin production is the cracking of petroleum feedstocks to olefins. The cracking of petroleum feedstocks is done through catalytic cracking, steam cracking, or some combination of the two processes. The olefins produced are generally light olefins, such as ethylene and propylene. There is a large market for the light olefin products of ethylene and propylene. As petroleum feedstocks from crude oil face increasing prices it is advantageous to provide for other sources of ethylene and propylene.

An ethylene plant involves a very complex combination of reaction and gas recovery systems. Feedstock is charged to a thermal cracking zone in the presence of steam at effective conditions to produce a pyrolysis reactor effluent gas mixture. The mixture is then stabilized and separated into purified components through a sequence of cryogenic and conventional fractionation steps. Ethylene and propylene yields from steam cracking and other processes may be improved using known methods for the metathesis or disproportionation of C4 and heavier olefins, in combination with a cracking step in the presence of a zeolitic catalyst, as described, for example, in U.S. Pat. Nos. 5,026,935 and 5,026,936.

The cracking of olefins in hydrocarbon feedstocks comprising C4 mixtures from refineries and steam cracking units is described in U.S. Pat. Nos. 6,858,133; 7,087,155; and 7,375,257.

Paraffin dehydrogenation represents an alternative route to light olefins and is described in U.S. Pat. No. 3,978,150 and elsewhere. More recently, the desire for alternative, non-petroleum based feeds for light olefin production has led to the use of oxygenates such as alcohols and, more particularly, methanol, ethanol, and higher alcohols or their derivatives. The alcohols, and in particular methanol, can be produced from other sources such as biomass and natural gas. The most common conversion of oxygenates to olefins is the production of light olefins from methanol, and one process is described in U.S. Pat. No. 5,914,433. The yield of light olefins from such a process may be improved using olefin cracking to convert some or all of the C4+ product of MTO in an olefin cracking reactor, as described in U.S. Pat. No. 7,268,265. Other processes for the generation of light olefins involve high severity catalytic cracking of naphtha and other hydrocarbon fractions. A catalytic naphtha cracking process of commercial importance is described in U.S. Pat. No. 6,867,341.

The process of converting oxygenates to olefins is an important process for utilizing oxygenates, such as methanol, and converting them to higher value products such as monomers for plastics, such as ethylene and propylene. The process of converting oxygenates to olefins is a catalytic process, and the catalyst is usually a molecular sieve catalyst. Among the molecular sieves that are useful for the catalytic process are ZSM-type molecular sieves, but more particularly, it has been found that silico-aluminophosphate (SAPO) molecular sieves work well in the process.

Even with the different methods of producing light olefins, the demand for ethylene and propylene continues to increase. Therefore, a need exists for new methods, catalysts and equipment that can increase light olefin yields from existing sources of both straight-run and processed hydrocarbon streams.

SUMMARY

The present invention provides a process for maintaining reaction selectivity and conversion of an MTO process.

A first embodiment of the invention is a process for generating olefins, comprising passing an oxygenate to a methanol to olefins reactor comprising a fluidized reactor bed with an methanol to olefins MTO catalyst to generate a reactor outlet stream comprising olefins and catalyst; separating the reactor outlet stream into a reaction effluent stream comprising olefins and a catalyst stream; passing the catalyst stream to a second reaction unit; passing the reaction effluent stream to a effluent stream separation unit to generate an olefins rich stream and an oxygenate rich stream; and passing the oxygenate rich stream to the second reaction unit. An embodiment of the invention is one, any or all of prior embodiments in this paragraph up through the first embodiment in this paragraph wherein the second reaction unit is a fluidized bed reactor and receives catalyst from the MTO reactor. An embodiment of the invention is one, any or all of prior embodiments in this paragraph up through the first embodiment in this paragraph wherein the MTO reactor comprises a fluidized reactor bed with an MTO catalyst and a dense phase catalyst section, and wherein the second reaction unit is the dense phase catalyst section. An embodiment of the invention is one, any or all of prior embodiments in this paragraph up through the first embodiment in this paragraph wherein the catalyst in the dense phase catalyst section is circulated to the fluidized reactor bed. An embodiment of the invention is one, any or all of prior embodiments in this paragraph up through the first embodiment in this paragraph further comprising passing the catalyst stream to a stripper, to generate a stripped catalyst stream comprising catalyst with adsorbed hydrocarbons and oxygenates removed. An embodiment of the invention is one, any or all of prior embodiments in this paragraph up through the first embodiment in this paragraph further comprising passing the stripped catalyst stream to a catalyst regeneration unit. An embodiment of the invention is one, any or all of prior embodiments in this paragraph up through the first embodiment in this paragraph wherein the oxygenate rich stream from the effluent separation unit comprises acetone and other by-product oxygenates from the MTO reactor. An embodiment of the invention is one, any or all of prior embodiments in this paragraph up through the first embodiment in this paragraph further comprising passing the catalyst stream to a stripper to generate a stripped catalyst stream.

A second embodiment of the invention is a process for generating olefins comprising passing an oxygenate to a methanol to olefins (MTO) reactor comprising a fluidized reactor bed with an MTO catalyst to generate a reactor outlet stream comprising olefins and catalyst; passing the reactor outlet stream into a first catalyst separation unit to generate a reaction effluent stream comprising olefins and oxygenates, and a catalyst stream; passing the catalyst stream to a regeneration unit to generate a regenerated catalyst stream; passing the reaction effluent stream to a effluent stream separation unit to generate an olefins rich stream and an oxygenate rich stream; passing the oxygenate rich stream to a second reactor using a portion of the regenerated catalyst stream to generate a second reactor process stream; and passing the second reactor process stream to a second catalyst separation unit. An embodiment of the invention is one, any or all of prior embodiments in this paragraph up through the second embodiment in this paragraph further comprising passing the catalyst stream to a stripping section to generate a spent catalyst stream having residual hydrocarbons and oxygenate compounds removed; and passing the spent catalyst stream to the regeneration unit. An embodiment of the invention is one, any or all of prior embodiments in this paragraph up through the second embodiment in this paragraph wherein the second catalyst separation unit is the first catalyst separation unit for the reactor outlet stream. An embodiment of the invention is one, any or all of prior embodiments in this paragraph up through the second embodiment in this paragraph wherein the second reactor is a fluidized bed reactor. An embodiment of the invention is one, any or all of prior embodiments in this paragraph up through the second embodiment in this paragraph wherein the second reactor is a riser reactor.

A third embodiment of the invention is a process for generating olefins comprising passing an oxygenate to a methanol to olefins (MTO) reactor comprising a fluidized reactor bed with an MTO catalyst to generate a reactor outlet stream comprising olefins and catalyst; passing the reactor outlet stream into a first catalyst separation unit to generate a reaction effluent stream comprising olefins and oxygenates, and a spent catalyst stream; passing a portion of the spent catalyst stream to a second reactor; passing the reaction effluent stream to an effluent stream separation unit to generate an olefins rich stream and an oxygenate rich stream; passing the oxygenate rich stream to the second reactor using a portion of the spent catalyst stream to generate a second reactor process stream; and passing the second reactor effluent to a second catalyst separation unit to generate a second reactor effluent stream comprising olefins and a second reactor catalyst stream. An embodiment of the invention is one, any or all of prior embodiments in this paragraph up through the third embodiment in this paragraph further comprising passing the spent catalyst stream to a stripping unit to generate a stripped spent catalyst stream; and passing the stripped spent catalyst stream to the second reactor. An embodiment of the invention is one, any or all of prior embodiments in this paragraph up through the third embodiment in this paragraph wherein the second reactor is a riser reactor. An embodiment of the invention is one, any or all of prior embodiments in this paragraph up through the third embodiment in this paragraph further comprising passing the second reactor catalyst stream to a regeneration unit. An embodiment of the invention is one, any or all of prior embodiments in this paragraph up through the third embodiment in this paragraph further comprising regenerating the second reactor catalyst stream to produce a regenerated catalyst stream; passing the regenerated catalyst stream to a second stripping unit to generate a fresh regenerated catalyst stream; and passing the fresh regenerated catalyst stream to the MTO reactor. An embodiment of the invention is one, any or all of prior embodiments in this paragraph up through the third embodiment in this paragraph further comprising recycling a portion of the spent catalyst stream to the MTO reactor fluidized bed. An embodiment of the invention is one, any or all of prior embodiments in this paragraph up through the third embodiment in this paragraph further comprising; passing the portion of recycled spent catalyst stream through a catalyst cooler to generate a cooled catalyst stream; and passing the cooled catalyst stream to the MTO reactor fluidized bed.

Other objects, advantages and applications of the present invention will become apparent to those skilled in the art from the following detailed description and drawings.

DETAILED DESCRIPTION

The production of light olefins from oxygenates, and in particular methanol, generate oxygenate byproducts. These byproducts can be recovered and recycled to the conversion reactor, and this increases the conversion rate of an oxygenate feed to a high purity light olefin product. Light olefins consist of ethylene and propylene.

In a commercial methanol to olefins (MTO) design, oxygenates are recycled to the MTO reactor, which results in a build up of concentration of oxygenates in the reactor recycle. As used hereinafter, the common term methanol to olefins, or MTO, is meant to refer to any oxygenate to olefins conversion process that can be covered by this disclosure. The build up is impacted by the extent that the oxygenates are converted with each pass through the MTO reactor. It has been found that some oxygenates concentrate to higher than previously thought, and adversely affect the expected conversion to be lower than previously predicted. In particular, the concentration of acetone in the recycle increases over time and this increases the acetone fed to the MTO reactor. The recycled oxygenates compete with the feed methanol for active catalyst sites, and the conversion of methanol to olefins. One method involving methanol to olefins includes the conversion of methanol to dimethyl ether (DME) and water, with a step of removing the water. The DME and methanol are then further converted to olefins in an MTO reactor. The present invention is intended to include such a configuration, where the oxygenate feed can be a methanol/DME feed to the MTO reactor.

It is desirable to pass recycled oxygenate by-products to a reactor, or to a location where the methanol/DME is low. This promotes a higher conversion of the recycled oxygenates, while preventing a reduction in the conversion of methanol/DME in the MTO reactor. An MTO reactor can then be operated to maximize the selectivity for light olefin production.

An enhanced conversion of oxygenate per pass of recycled oxygenates would lower the amount of recycled oxygenate competition for catalyst sites and allow for a higher overall methanol and DME concentration in the feed to the reactor.

Figure 1:
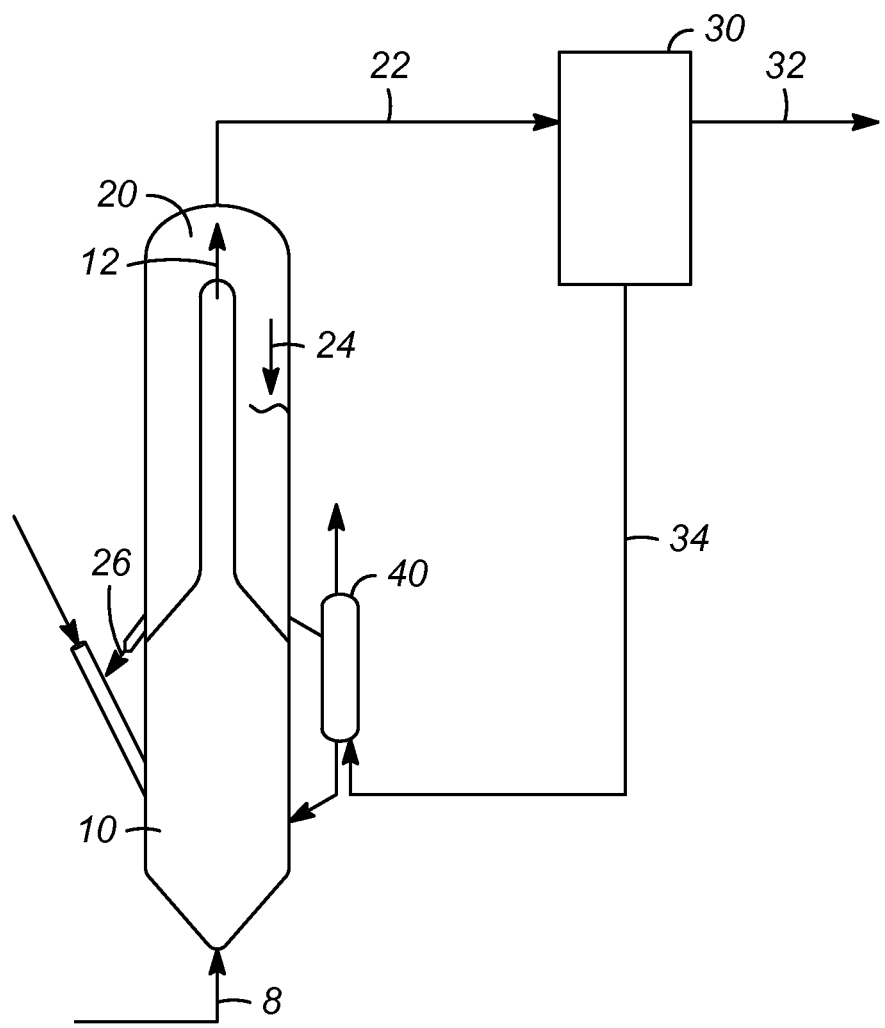
FIG. 1 is one embodiment of the process for recycling oxygenates to an MTO reactor system.

One embodiment provides for a smaller fluidized bed reactor integrated into the MTO reactor system. The process can be seen in FIG. 1, wherein an oxygenate feed stream 8 is passed to an MTO reactor 10. The reactor 10 is a fluidized bed reactor and includes an MTO catalyst to generate a reactor outlet stream 12 comprising olefins and catalyst. The reactor outlet stream 12 is separated in a separation section 20 of the MTO reactor system. The outlet stream is separated into a reaction effluent stream 22 and a catalyst stream 24. The catalyst stream 24 can recycle the catalyst to the MTO reactor 10, or a portion of the catalyst can be passed out in a stream 26 which is passed to a catalyst regeneration unit. The reaction effluent stream 22 is passed to an effluent stream separation unit 30 to generate an olefins rich stream 32 and an oxygenate rich stream 34. The catalyst stream 24 is passed to a second reactor unit 40. The oxygenate rich stream 34 is passed as a recycle stream to the second reactor unit 40. The oxygenate rich stream is therefore processed in a reaction zone such that the recycled oxygenates do not compete with the methanol/DME from the oxygenate feedstream 8 to the MTO reactor 10.

The MTO reactor system is a fluidized bed reactor system, and the catalyst is cycled through the MTO reactor and the second reactor unit, where catalyst separated from the MTO reactor is passed through the second reactor unit before passing to the MTO reactor, or before passing a portion of the catalyst from the second reactor unit to a catalyst regeneration unit. Other types of reactors that include cycling catalyst through the reactor can be included in this description. The effluent separation unit 30 can comprise a system of fractionation columns and or absorbers for the separation of the hydrocarbons from the oxygenates.

Figure 2:
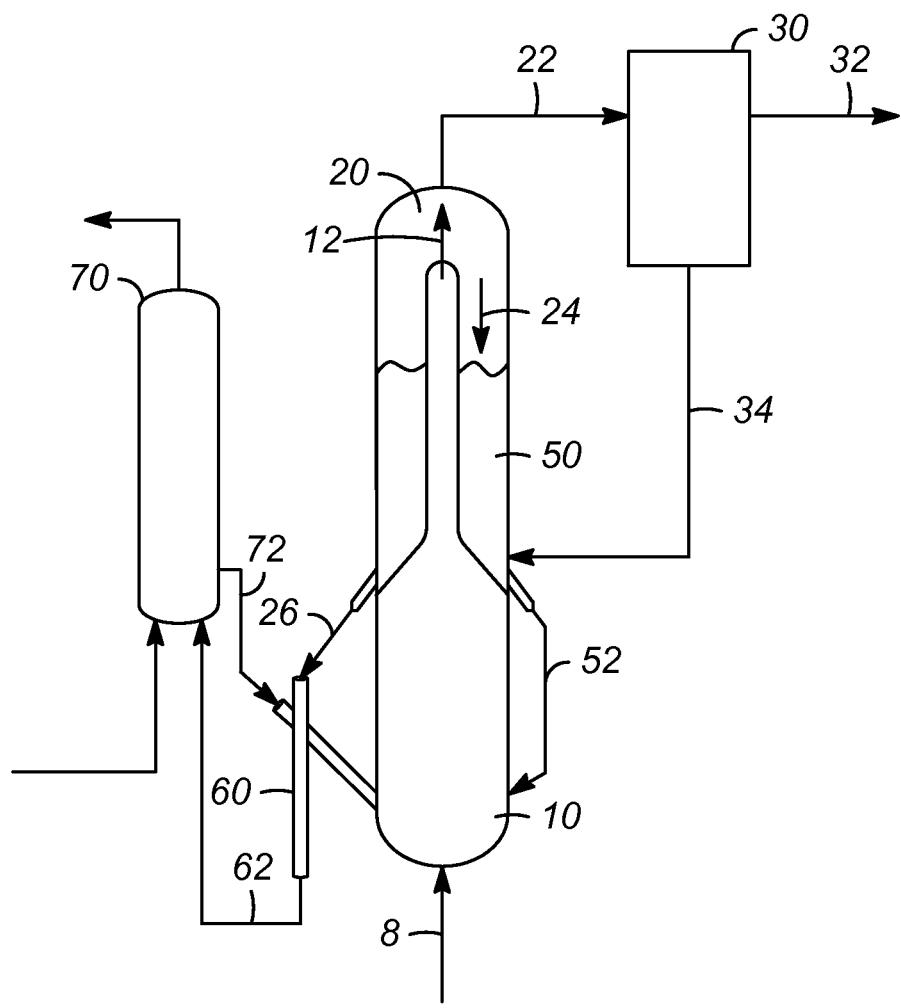
FIG. 2 is a second embodiment of the process for recycling oxygenates to an MTO reactor system.

In one embodiment, the process is similar to that described above, but is shown in FIG. 2. An oxygenate feed 8 is passed to an MTO reactor 10, to generate an MTO reactor outlet stream 12 comprising olefins and catalyst. The reactor outlet stream 12 is separated in a separation section 20 of the MTO reactor system. The outlet stream is separated into a reaction effluent stream 22 and a catalyst stream 24. The reaction effluent stream 22 is passed to an effluent stream separation unit 30 to generate an olefins rich stream 32 and an oxygenate rich stream 34. The oxygenate rich stream comprises acetone and other oxygenates formed in the MTO reactor. The oxygenate rich stream can also include oxygenates such as methanol to increase solubility of oxygenates in an aqueous phase for separation from the reaction effluent stream. The catalyst after separation from the reaction effluent stream settles to form a dense phase region 50. The oxygenate rich stream 34 is passed to the dense phase region 50 to utilize catalyst that has been carried out of the MTO reactor. This dense phase region 50 can act as a second reactor unit, wherein further reactions are carried out in the conversion of recycled oxygenates to olefins. The catalyst from the dense phase region 50 can be passed out to form a catalyst circulation stream 52, and the catalyst circulation stream 52 is passed to the MTO reactor 10.

A portion of the catalyst in the circulation loop for the MTO reactor is drawn off for passing to a regeneration unit. The portion drawn off 26 is passed to a stripper 60, to generate a stripped catalyst stream 62 to remove residual oxygenates, hydrocarbons and reactants left adsorbed onto the catalyst. The stripped catalyst stream 62 is passed to the regeneration unit 70 where the catalyst is regenerated and the regenerated catalyst is returned 72 to the MTO reactor 10. The regeneration comprises combustion of carbon deposits formed on the catalyst during the oxygenate to olefins conversion reaction. The catalyst circulation loop can optionally include a catalyst cooler for regulating the catalyst temperature in the MTO reactor.

Figure 3:
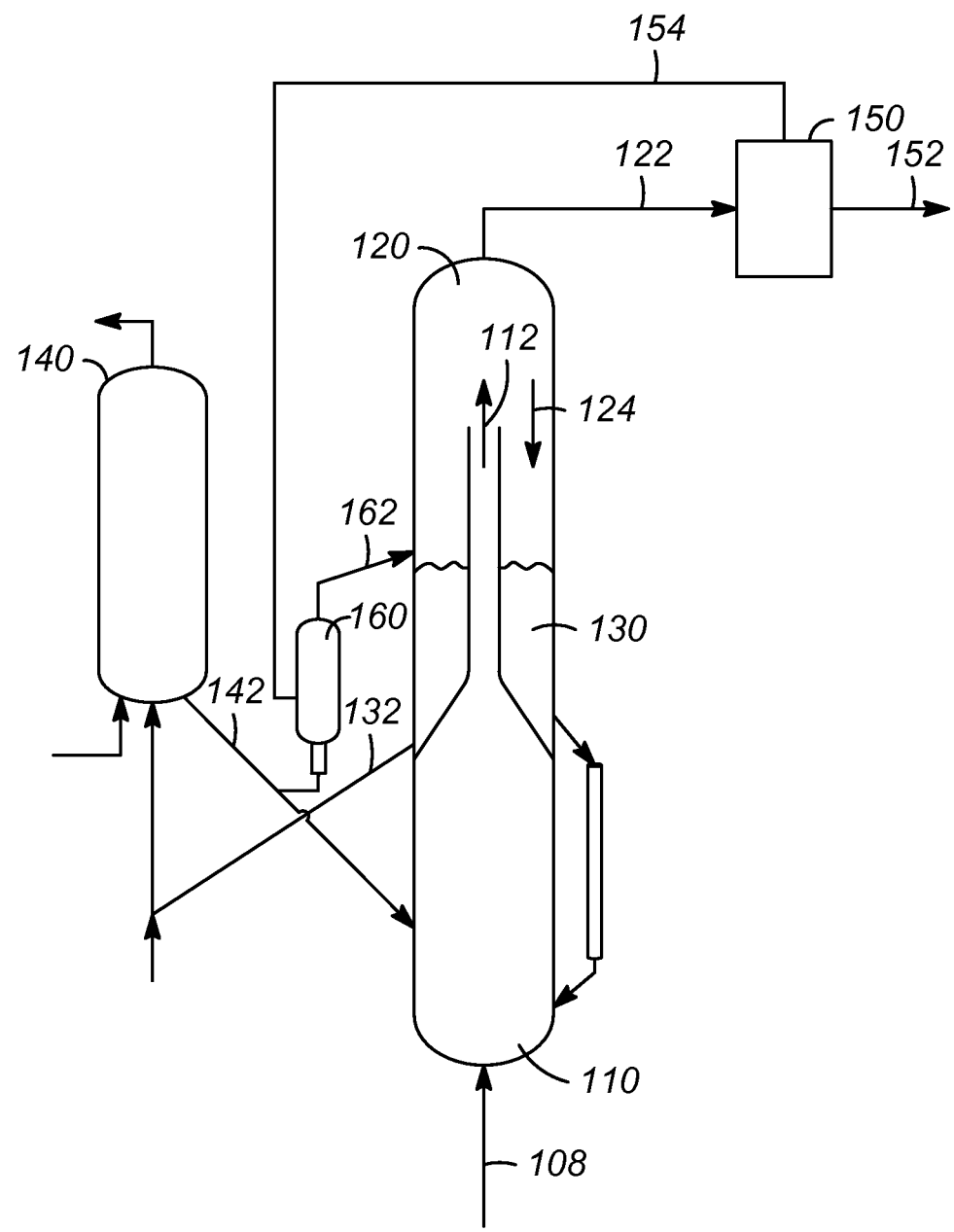
FIG. 3 is a third embodiment of the process for recycling oxygenates to an MTO reactor system.

One embodiment provides for utilizing regenerated catalyst to process the recycled oxygenates as the catalyst cycles through the MTO reactor/regenerator system. This embodiment is demonstrated by FIG. 3, where an oxygenate feed 108 is passed to an MTO reactor 110. The MTO reactor comprises a fluidized reactor bed with an MTO catalyst to generate a reactor outlet stream 112 comprising catalyst and olefins. The reactor outlet stream 112 passed to a first catalyst separation zone 120 to generate a reaction effluent stream 122 and a catalyst stream 124. The catalyst stream 124 accumulates in a holding zone 130, where the catalyst can be cycled through the MTO reactor 110. A portion of the catalyst 132 is passed from the catalyst holding zone 130 to a regeneration unit 140 to generate a regenerated catalyst stream 142. The reaction effluent stream 122 is passed to an effluent stream separation unit 150 to generate an olefins rich stream 152 and an oxygenate rich stream 154. The oxygenate rich stream 154 and a portion of regenerated catalyst stream 142 is passed back to the second reactor 160 and generates a second reactor process stream 162. The second reactor process stream 162 is passed to a catalyst separation unit to disengage the product from the catalyst. In one embodiment, the second process stream 162 is passed to the catalyst separation zone 120 where the product stream from the second reactor merges with the MTO reaction effluent stream 122.

In an alternative, the catalyst separation unit for the second reactor 160 can be a separate unit from the catalyst separation zone 120. The second reactor can be a fluidized bed reactor or a riser reactor. The catalyst after leaving the second reactor 160 is preferably passed to the MTO reactor system, where the catalyst can cycle through the MTO reactor. The catalyst cycles through the MTO reactor and is separated from the process stream, with a portion of the catalyst stream passed to the regeneration unit. The rate of draw-off of catalyst passed to the regeneration unit is determined by the amount of coking on the catalyst. In one embodiment, the portion of catalyst drawn-off for return to the regeneration unit is passed through a spent catalyst stripping section to remove residual hydrocarbons and residual oxygenate compounds to form a stripped catalyst stream. The stripped catalyst stream is then passed to the regeneration unit to create a regenerated catalyst stream.

Figure 4:
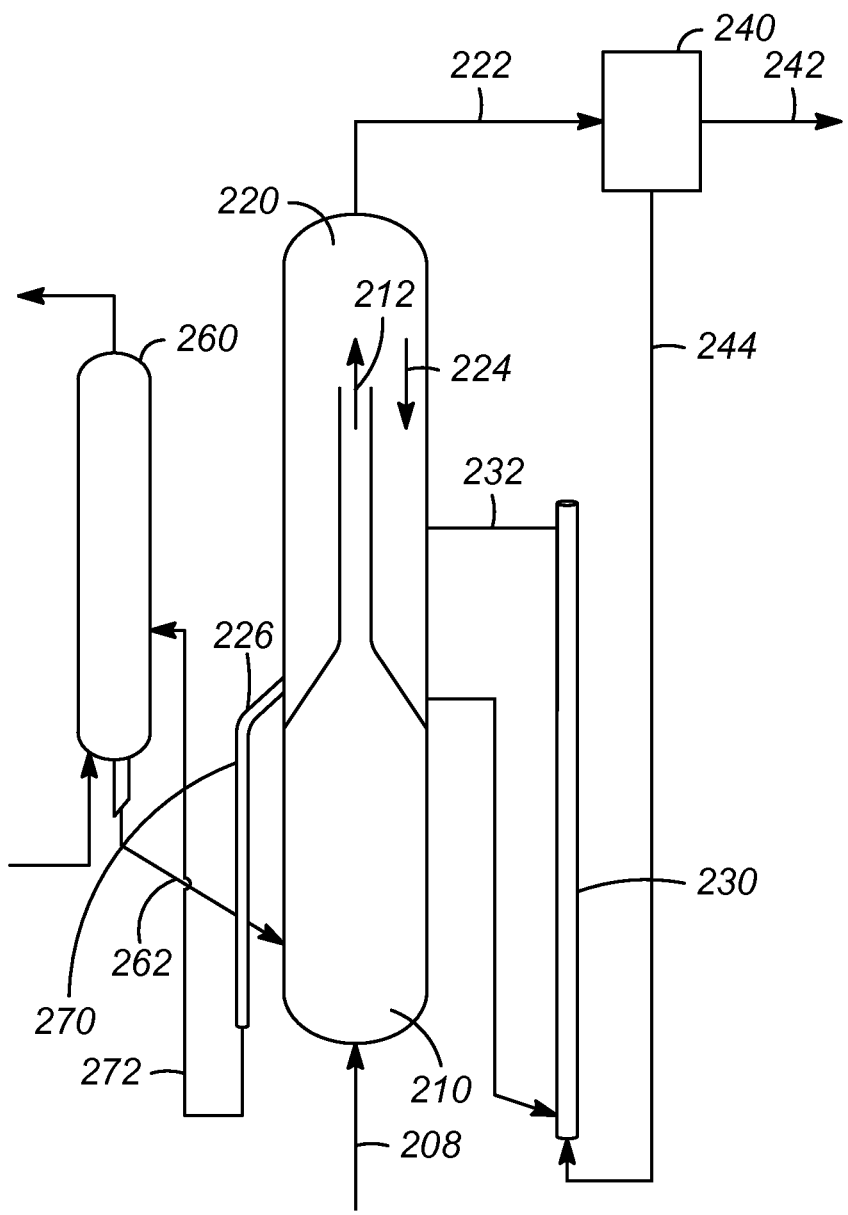
FIG. 4 is a fourth embodiment of the process for recycling oxygenates to an MTO reactor system.

In another embodiment, the process comprises utilizing catalyst that includes partially spent catalyst for converting recycled oxygenates. The process is shown in FIG. 4, where an oxygenate feed 208 is passed to an MTO reactor 210, comprising a fluidized reactor bed. The MTO reactor generates an outlet stream 212 that comprises olefins, unreacted oxygenates, oxygenate by-products and catalyst. The outlet stream 212 passes to a catalyst separation zone 220 wherein the catalyst and process stream are separated into a reaction effluent stream 222 and a catalyst stream 224. The catalyst stream 224 comprises partially spent catalyst, and a portion is passed to a riser reactor unit 230. The reaction effluent stream 222 is passed to an effluent separation unit 240 which generates an olefin rich stream 242 and an oxygenate rich stream 244. The oxygenate rich stream 244 is passed to the riser reactor 230 and generate a riser reactor effluent stream 232. The riser reactor effluent stream 232 is passed to a catalyst separation unit to generate a riser reactor product stream and a riser reactor catalyst stream. In one embodiment, the riser reactor effluent stream 232 is passed to the catalyst separation zone 220 in the MTO reactor system. As an optional alternative, a second catalyst separation zone can receive the riser reactor effluent stream.

The riser reactor product stream is passed with the MTO reaction effluent stream to the effluent separation unit for olefins recovery. The catalyst collected in the catalyst separation zone is cycled through the MTO reactor, and a portion of the catalyst is passed as a spent catalyst stream 226 to a regeneration unit 260. The regeneration unit 260 creates a regenerated catalyst stream 262 and passes the regenerated catalyst to the MTO reactor 210. In one embodiment, the spent catalyst stream 226 is passed to a stripping unit 270 to generate a stripped catalyst stream 272 and the stripped catalyst stream 272 is passed to the regeneration unit 260. The process also includes, as an option, catalyst coolers, wherein the catalyst recycled from the regeneration unit 260 is passed through a catalyst cooler to deliver a cooled, regenerated catalyst to the MTO reactor 210. Catalyst coolers can also be included in the catalyst loops wherein catalyst collected from the catalyst separation zone 220 is passed through a catalyst cooler before passing to the MTO reactor inlet.

An option also includes using a fixed bed reactor for the second reactor. A fixed bed reactor system for the second reactor allows for the use of a different catalyst, and the choice of catalyst can be tailored to the oxygenate by-products generated by the MTO reactor system.

The feedstream to the reactor is preferably preheated to a temperature in the range between 120° C. and about 210° C. A preferred preheated feedstream temperature is in the range of 180° C. and 210° C., with the feedstream temperature held below or at 210° C. to minimize thermal decomposition of the feedstream.

Each reactor stage is operated at a temperature in the range from 200° C. to 700° C., with a preferred temperature range of 300° C. to 600° C., and a more preferred temperature range of 400° C. to 550° C. The reaction conditions of each reactor stage includes a pressure in the range of 0.1 kPa to 10 MPa, with a preferred pressure in the range of 100 kPa to 800 kPa, and more preferably in the range 170 kPa to 800 kPa.

The choice of operating pressure is also balanced with the ability to flow the reactants through the two stage reactor system without additional intermediate, or downstream compressors. The feedstream is an oxygenate, and a preferred feedstream is methanol, or other alcohols. To obtain the desired operating pressures, the feedstream can be pumped as a liquid to a selected pressure range, and then preheated to a selected temperature range. The preheating of the feedstream can vaporize the feedstream such that the reactor is operated with gas phase reactants.

The process comprises continuously regenerating the catalyst, and cycling the catalyst through the two reactor stage beds. The catalyst in the regenerator is heated to a temperature sufficient to burn off the coke that is deposited on the catalyst during the oxygenate conversion. In a preferred embodiment, the catalyst is regenerated by burning off coke, or carbonaceous, deposits accumulated during the reactions. An oxidizing gas is passed to the regenerator to oxidize the coke and regenerate the catalyst. The preferred oxidizing gas is air. Temperatures will typically be in the 500° C. to 700° C. range, and return a catalyst that can be too hot for use in the reactor.

Any catalyst used for the conversion of oxygenates to olefins would be applicable for this process. Catalysts used in oxygenate to olefins conversion includes catalysts such as silicoaluminophosphate molecular sieves, or SAPO catalysts, or a molecular sieve catalyst such as ZSM-5.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for generating olefins, comprising:
    passing an oxygenate comprising methanol to a methanol to olefins (MTO) reactor comprising a first fluidized reactor bed unit with an MTO catalyst to generate a reactor outlet stream comprising olefins and catalyst;
    separating the reactor outlet stream into a reaction effluent stream comprising olefins and a catalyst stream;
    passing the reaction effluent stream to an effluent stream separation unit to generate an olefins rich stream and an oxygenate rich stream comprising acetone and other by-product oxygenates formed from the first MTO reactor; and
    passing a first portion of the catalyst stream and the oxygenate rich stream to a second reaction unit to generate a second reactor effluent stream comprising olefins, wherein the second reaction unit comprises a dense phase catalyst bed.

2. The process of claim 1 wherein the second reaction unit is a fluidized bed reactor and receives catalyst from the MTO reactor.

3. The process of claim 1 wherein the MTO reactor comprises a dense phase catalyst section, and wherein the second reaction unit is the dense phase catalyst section.

4. The process of claim 3 wherein the catalyst in the dense phase catalyst section is circulated to the first fluidized reactor bed unit.

5. The process of claim 1 further comprising passing a second portion of the catalyst stream to a stripper, to generate a stripped catalyst stream comprising catalyst with adsorbed oxygenates and hydrocarbons removed.

6. The process of claim 5 further comprising passing the stripped catalyst stream to a catalyst regeneration unit.

7. The process of claim 3 further comprising passing a second portion of the catalyst stream to a stripper to generate a stripped catalyst stream.

8. A process for generating olefins comprising:
    passing an oxygenate comprising methanol to a methanol to olefins (MTO) reactor comprising a fluidized reactor bed with an MTO catalyst to generate a reactor outlet stream comprising olefins and catalyst;
    passing the reactor outlet stream into a first catalyst separation unit to generate a reaction effluent stream comprising olefins and oxygenates, and a catalyst stream;
    passing the catalyst stream to a regeneration unit to generate a regenerated catalyst stream;
    passing the reaction effluent stream to an effluent stream separation unit to generate an olefins rich stream and an oxygenate rich stream comprising acetone and other by-product oxygenates formed from the MTO reactor;
    passing the oxygenate rich stream and a portion of the regenerated catalyst stream to a second reactor to generate a second reactor process stream, wherein the second reactor comprises a dense phase bed; and
    passing the second reactor process stream to the first catalyst separation unit.

9. The process of claim 8 further comprising:
    passing the catalyst stream to a stripping section to generate a spent catalyst stream having residual hydrocarbons and oxygenate compounds removed; and
    passing the spent catalyst stream to the regeneration unit.

10. The process of claim 8 wherein the second catalyst separation unit is the first catalyst separation unit for the reactor outlet stream.

11. The process of claim 8 wherein the second reactor is a fluidized bed reactor.

12. The process of claim 8 wherein the second reactor is a riser reactor.

13. A process for generating olefins comprising:
    passing an oxygenate comprising methanol to a methanol to olefins (MTO) reactor comprising a fluidized reactor bed with an MTO catalyst to generate a reactor outlet stream comprising olefins and catalyst;
    passing the reactor outlet stream into a first catalyst separation unit to generate a reaction effluent stream comprising olefins and oxygenates, and a spent catalyst stream;

passing a portion of the spent catalyst stream to a second reactor, wherein the second reaction reactor comprises a dense phase catalyst bed:

passing the reaction effluent stream to an effluent stream separation unit to generate an olefins rich stream and an oxygenate rich stream comprising acetone and other by-product oxygenates formed in the first MTO reactor;

passing the oxygenate rich stream to the second reactor and contacting the portion of the spent catalyst stream to generate a second reactor process stream; and passing the second reactor effluent to a second catalyst separation unit to generate a second reactor effluent stream comprising olefins and a second reactor catalyst stream.

14. The process of claim 13 further comprising:
passing the spent catalyst stream to a stripping unit to generate a stripped spent catalyst stream; and
passing the stripped spent catalyst stream to the second reactor.

15. The process of claim 13 wherein the second reactor is a riser reactor.

16. The process of claim 13 further comprising passing the second reactor catalyst stream to a regeneration unit.

17. The process of claim 16 further comprising:
regenerating the second reactor catalyst stream to produce a regenerated catalyst stream;
passing the regenerated catalyst stream to a second stripping unit to generate a fresh regenerated catalyst stream; and
passing the fresh regenerated catalyst stream to the MTO reactor.

18. The process of claim 13 further comprising:
recycling a portion of the spent catalyst stream to the MTO reactor fluidized bed.

19. The process of claim 18 further comprising;
passing the portion of recycled spent catalyst stream through a catalyst cooler to generate a cooled catalyst stream; and
passing the cooled catalyst stream to the MTO reactor fluidized bed.

* * * * *